(12) United States Patent
Horng et al.

(10) Patent No.: US 9,423,496 B2
(45) Date of Patent: Aug. 23, 2016

(54) WIRELESS DETECTION DEVICES AND WIRELESS DETECTION METHODS

(71) Applicant: NATIONAL SUN YAT-SEN UNIVERSITY, Kaohsiung (TW)

(72) Inventors: Tzyy-Sheng Horng, Kaohsiung (TW); Fu-Kang Wang, Kaohsiung (TW); Kang-Chun Peng, Kaohsiung (TW)

(73) Assignee: NATIONAL SUN YAT-SEN UNIVERSITY, Kaohsiung (TW)

( * ) Notice: Subject to any disclaimer, the term of this patent is extended or adjusted under 35 U.S.C. 154(b) by 289 days.

(21) Appl. No.: 13/787,699

(22) Filed: Mar. 6, 2013

(65) Prior Publication Data

US 2013/0338515 A1 Dec. 19, 2013

(30) Foreign Application Priority Data

Jun. 14, 2012 (TW) .............................. 101121230 A (51) Int. Cl.

| | |
|---|---|
| *G01S 13/04* | (2006.01) |
| *G01S 13/08* | (2006.01) |
| *G01S 7/41* | (2006.01) |
| *G01S 13/34* | (2006.01) |
| *G01S 13/88* | (2006.01) |
| *A61B 5/024* | (2006.01) |
| *A61B 5/08* | (2006.01) |

(52) U.S. Cl.
CPC ................ *G01S 13/08* (2013.01); *G01S 7/415* (2013.01); *G01S 13/34* (2013.01); *G01S 13/888* (2013.01); *A61B 5/024* (2013.01); *A61B 5/0816* (2013.01)

(58) Field of Classification Search
CPC ...... G01S 13/56; G01S 13/888; G01S 13/08; G01S 7/415
USPC ......................................... 342/118, 128–131
See application file for complete search history.

(56) References Cited

U.S. PATENT DOCUMENTS

| | | | | |
|---|---|---|---|---|
| 5,325,095 A | * | 6/1994 | Vadnais .............. | G01S 13/0209 342/129 |
| 5,982,321 A | * | 11/1999 | Iihoshi .................... | G01S 13/42 342/128 |

(Continued)

OTHER PUBLICATIONS

Fu-Kang Wang; Chien-Jung Li; Chieh-Hsun Hsiao; Tzyy-Sheng Horng; Jenshan Lin; Kang-Chun Peng; Je-Kuan Jau; Jian-Yu Li; Cheng-Chung Chen, "A Novel Vital-Sign Sensor Based on a Self-Injection-Locked Oscillator," Microwave Theory and Techniques, IEEE Transactions on , vol. 58, No. 12, pp. 4112,4120, Dec. 2010.*

*Primary Examiner* — Jack W Keith
*Assistant Examiner* — Marcus Windrich
(74) *Attorney, Agent, or Firm* — Pai Patent & Trademark Law Firm; Chao-Chang David Pai (57) ABSTRACT

A wireless detection device is provided, comprising a voltage control oscillation unit, a transceiving unit, demodulation unit and processing unit. The voltage control oscillation unit generates different oscillation signals according to analog control voltages and corresponding injection signals. The transceiving unit outputs first wireless signals to a predetermined area according to the oscillation signals and receives second wireless signals generated by reflection of the first wireless signals to generate the injection signal. The demodulation unit demodulates the oscillation signals into first voltage signals. The processing unit subtracts the corresponding analog control voltages from the first voltage signals to generate second voltage signals, and when the variation of the second voltage signals exceeds a predetermined value on a target frequency in frequency domain, the processing unit calculates a real distance between an object and the transceiving unit.

12 Claims, 11 Drawing Sheets

(56) References Cited

U.S. PATENT DOCUMENTS

| | | | | |
|---|---|---|---|---|
| 7,916,066 B1* | 3/2011 | Osterweil | ............. | A61B 5/1117<br>340/573.1 |
| 2005/0073424 A1* | 4/2005 | Ruoss | ................. | A61B 5/0507<br>340/686.6 |
| 2006/0061504 A1* | 3/2006 | Leach | ....................... | G01S 7/41<br>342/22 |
| 2009/0262006 A1* | 10/2009 | McNeill | .................... | G01S 7/35<br>342/22 |
| 2009/0278728 A1* | 11/2009 | Morgan | ............... | A61B 5/0205<br>342/115 |
| 2010/0026550 A1* | 2/2010 | Rosenbury | ......... | A61B 5/02438<br>342/22 |
| 2011/0279275 A1* | 11/2011 | Horng | .................. | A61B 5/0205<br>340/573.1 |

\* cited by examiner

WIRELESS DETECTION DEVICES AND WIRELESS DETECTION METHODS

CROSS REFERENCE TO RELATED APPLICATIONS

This Application claims priority of Taiwan Patent Application No. 101121230, filed on Jun. 14, 2012, the entirety of which is incorporated by reference herein.

BACKGROUND OF THE INVENTION

1. Field of the Invention

The disclosure relates generally to detection devices, and more particularly, relates to wireless detection devices.

2. Description of the Related Art

In recent years, home security has become more important. However, when people are inside a house, the people often do not know whether there is someone close to the house or hiding behind the wall. Accordingly, the people cannot react immediately, such as calling the police or security. Also, there is no device which can effectively detect hidden people. Therefore, wireless detection devices and wireless detection methods are needed to overcome these problems.

BRIEF SUMMARY OF THE INVENTION

In light of the previously described problems, the invention provides a wireless detection device, comprising: a voltage control oscillation unit, generating a plurality of oscillation signals with different frequencies according to analog control voltages and corresponding injection signals; a transceiving unit, outputting a plurality of first wireless signals to a predetermined area according to the oscillation signals, and receiving second wireless signals generated by reflection of the first wireless signals to generate the injection signals; a demodulation unit, configured to demodulate the oscillation signals into first voltage signals; and a processing unit, subtracting the corresponding analog control voltages from the first voltage signals to generate second voltage signals, wherein when the variation of the second voltage signals exceeds a predetermined value on a target frequency in frequency domain, the processing unit calculates a real distance between an object and the transceiving unit.

The invention also provides a wireless detection method, comprising: generating a plurality of oscillation signals with different frequencies according to analog control voltages outputted by a signal generating unit and corresponding injection signals; outputting a plurality of first wireless signals to a predetermined area according to the oscillation signals, and receiving second wireless signals generated by reflection of the first wireless signals to generate the injection signals; generating second voltage signals by subtracting the corresponding analog control voltages from the first voltage signals, wherein the first voltage signals is demodulated from the oscillation signals; and when the variation of the second voltage signals exceeds a predetermined value on a target frequency in frequency domain, calculating a real distance between an object and a transceiving unit according to the target frequency by a processing unit.

BRIEF DESCRIPTION OF DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
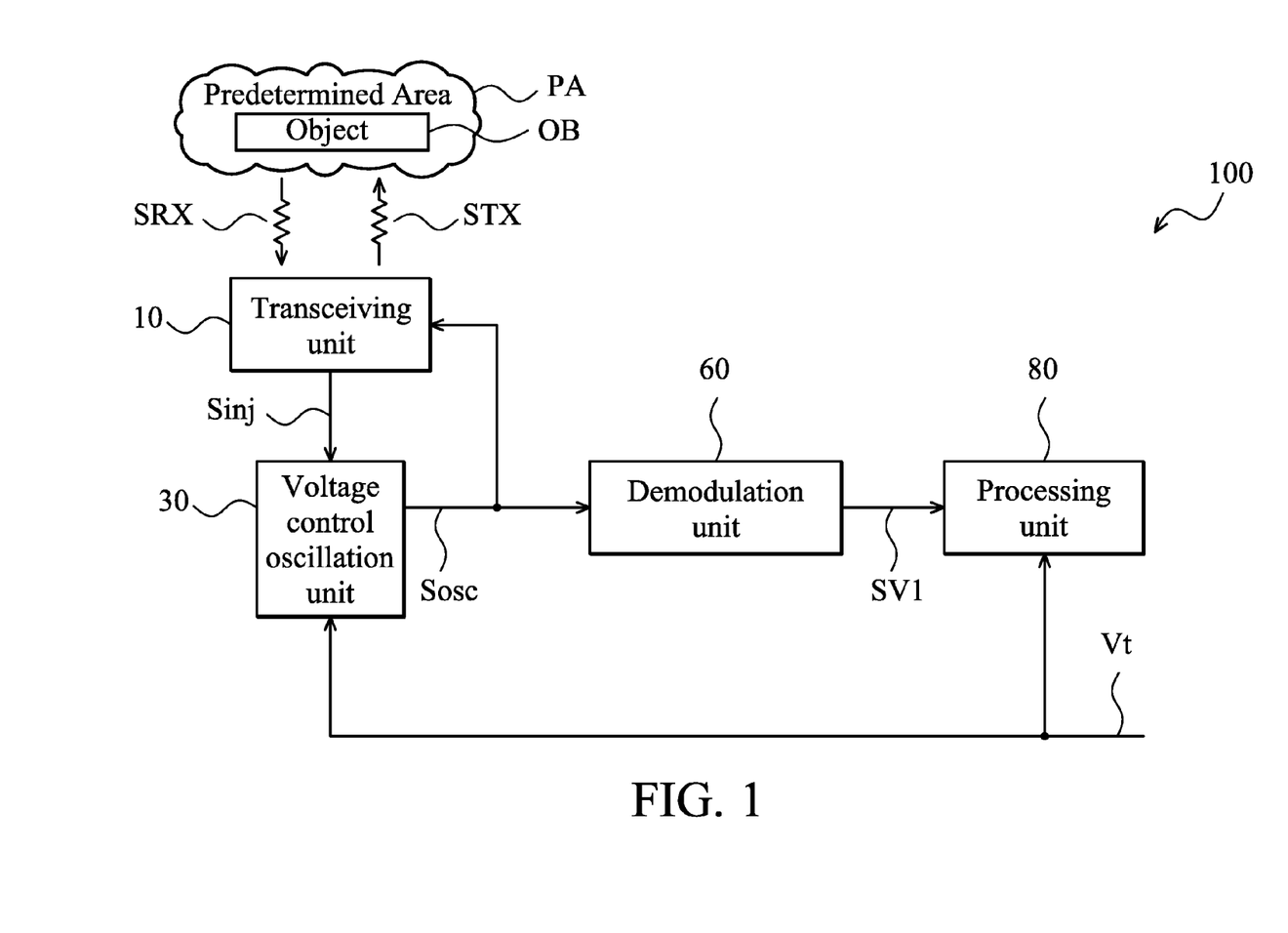
FIG. 1 is a schematic diagram illustrating a wireless detection device of the disclosure.

FIG. 1 is a schematic diagram illustrating a wireless detection device of the disclosure. As shown in FIG. 1, the wireless detection device 100 comprises a transceiving unit 10, a voltage control oscillation unit 30, a demodulation unit 60 and a processing unit 80. In more detail, the voltage control oscillation unit 30 generates a plurality of oscillation signals Sosc with different frequencies according to a plurality of analog control voltages Vt and corresponding injection signals Sinj. The transceiving unit 10 outputs a plurality of wireless signals STX to a predetermined area PA according to the oscillation signals Sosc, and receives wireless signals SRX generated by reflection of the wireless signals STX to generate the injection signals Sinj.

In an embodiment of the present invention, when the voltage control oscillation unit 30 is interfered by the injection signal Sinj, the voltage control oscillation unit 30 performs a self-injection lock operation to generate the oscillation signal Sosc. Also, the operation frequency of the voltage control oscillation unit 30 varies within a frequency band, so that the frequency offset caused by the wireless signal SRX varies accordingly, and the frequency variation rate is directly proportional to the delay time of the self-injection lock path.

The demodulation unit 60 is configured to demodulate the oscillation signals Sosc into first voltage signals SV1. The processing unit 80 subtracts the corresponding analog control voltages Vt from the first voltage signals SV1 to generate a plurality second voltage signals. When the variation of the second voltage signals exceeds a predetermined value on a target frequency in frequency domain, the processing unit 80 calculates a real distance between an object OB and the transceiving unit 10.

Figure 2:
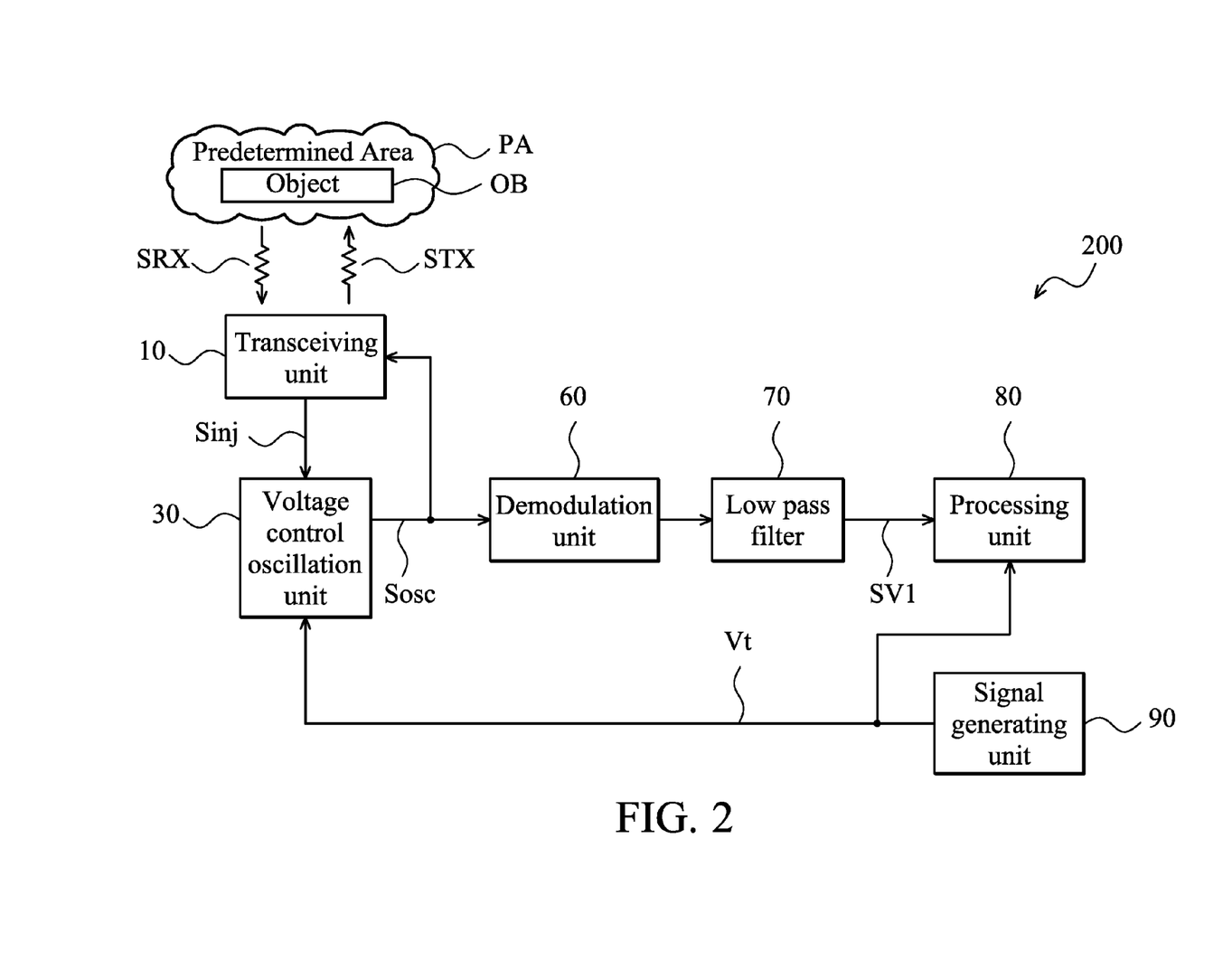
FIG. 2 is another schematic diagram illustrating a wireless detection device of the disclosure.

FIG. 2 is another schematic diagram illustrating a wireless detection device of the disclosure. As shown in FIG. 2, the wireless detection device 200 is similar to the wireless detection device 100, and the difference is that the wireless detection device 200 further comprises a low pass filter 70 and a signal generating unit 90. The low pass filter 70 is connected between the demodulation unit 60 and the processing unit 80, and configured to filter high frequency noise. The signal generating unit 90 is configured to generate the analog control voltages Vt to the voltage control oscillation unit 30 and the processing unit 80.

Figure 3:
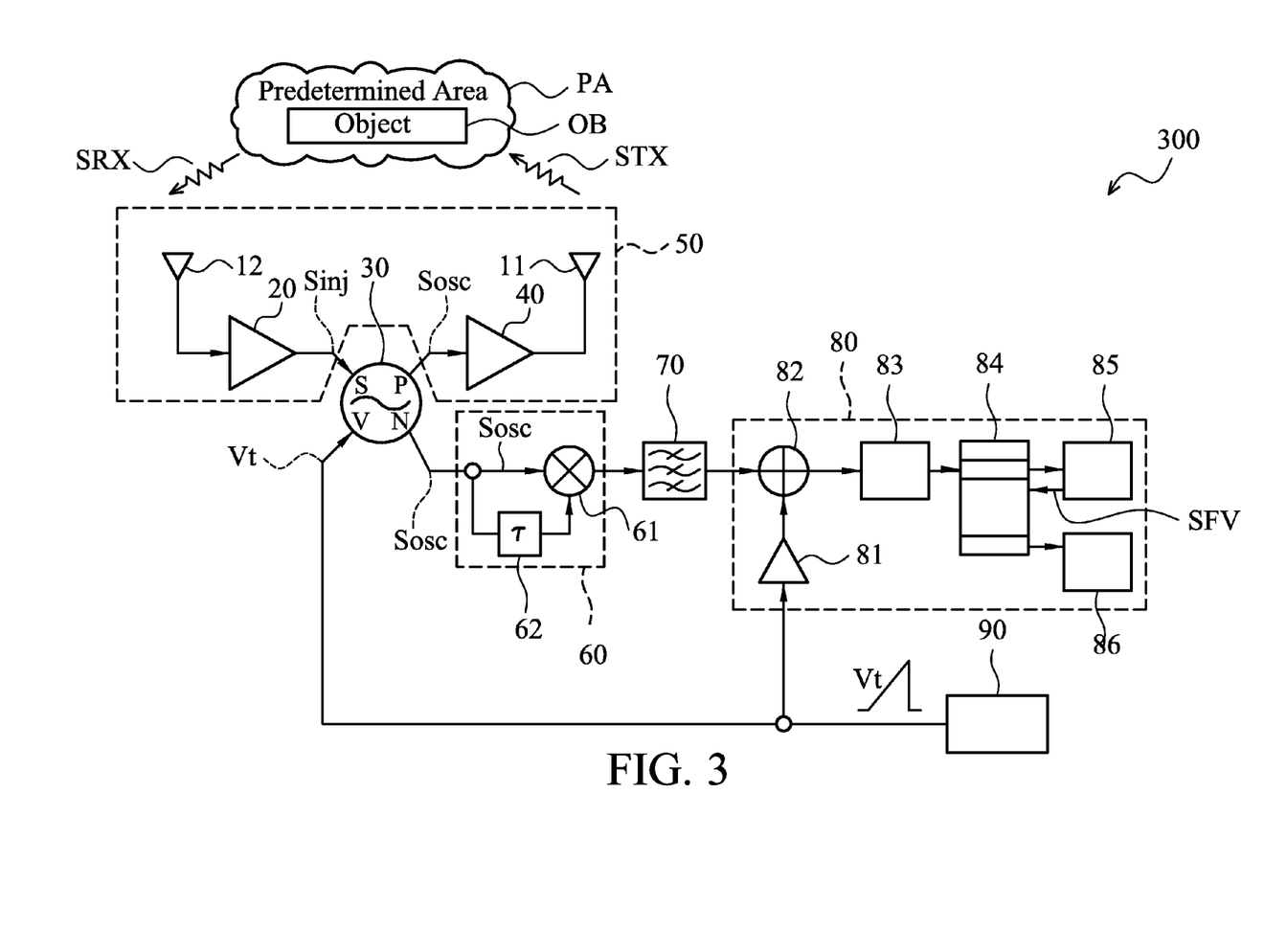
FIG. 3 is another schematic diagram illustrating a wireless detection device of the disclosure.

FIG. 3 is another schematic diagram illustrating a wireless detection device of the disclosure. As shown in FIG. 3, the wireless detection device 300 is the same as the wireless detection device 200. The transceiving unit 10 comprises an antenna 11, an antenna 12, an amplifier 20 and an amplifier 40. In more detail, the antenna 11 is configured to output the wireless signals STX to the object OB. The antenna 12 is configured to receive the wireless signals SRX. The amplifier 20 is connected between the antenna 12 and the voltage control oscillation unit 30, and configured to amplify the wireless signals SRX into the injection signals Sinj, wherein the amplifier 20 can be a low noise amplifier. The amplifier 40 is connected between the antenna 11 and the voltage control oscillation unit 30, and configured to amplify the oscillation signals Sosc into the wireless signals STX, wherein the amplifier 40 can be a power amplifier.

In some embodiments, the transceiving unit 10 only comprises an antenna 11 and a bidirectional amplifier, and the antenna 11 can output the wireless signals STX to the object OB and receive the wireless signals SRX. The bidirectional amplifier is connected between the antenna 11 and the voltage control oscillation unit 30, amplifies the wireless signals SRX into the injection signals Sinj, and amplifies the oscillation signals Sosc into the wireless signals STX. Therefore, the injection signals Sinj and the oscillation signals Sosc use the same transmission path. In some embodiments, the transceiving unit 10 only comprises an antenna 11. The antenna 11 is configured to output the wireless signals STX to the object OB, and receive the wireless signals SRX to output the injection signals Sinj. Therefore, the injection signals Sinj and the oscillation signals Sosc use the same transmission path.

The demodulation unit 60 comprises a delayer 62 and a mixer 61. In more detail, the delayer 62 is connected to the voltage control oscillation unit 30, and configured to delay the oscillation signals Sosc. The mixer 61 is connected to the voltage control oscillation unit 30 and the delayer 62, and configured to generate the first voltage signals SV1 by mixing the oscillation signals Sosc and the oscillation signals SV1. The low pass filter 70 is connected between the demodulation unit 60 and the processing unit 80, and configured to filter a high frequency noise from the oscillation signals SV1.

The processing unit comprises an amplifier 81, a subtractor 82, a subtractor 85, a calculating unit 83, a calculating unit 86 and a storage unit 84. In more detail, the amplifier 81 is connected to the signal generating unit 90, and configured to amplify the analog control voltages Vt. The subtractor 82 is coupled to the calculating unit 81, and configured to subtract the corresponding analog control voltages Vt from the first voltage signals SV1 to generate the second voltage signals SV2. The calculating unit 83 is coupled to the subtractor 82, and configured to transform the second voltage signals SV2 into frequency domain. The storage unit 84 is configured to store spectrums of the detected second voltage signals SV2 at different times. The subtractor 85 is coupled to the storage unit 84, and configured to obtain a difference between the second voltage signals SV2 to generate a spectrum variation signal SFV, wherein the spectrum variation signal SFV comprises information of the target frequency. The processing unit 80 calculates the real distance according to the target frequency, and the storage unit 84 is configured to store the detected real distances at different times. The calculating unit 86 performs Fourier transform to the real distance to obtain an oscillation frequency (variation frequency) of the object OB. In an embodiment of the present invention, the calculating unit 83 and the calculating unit 86 can be Fourier transformer.

Figure 4:
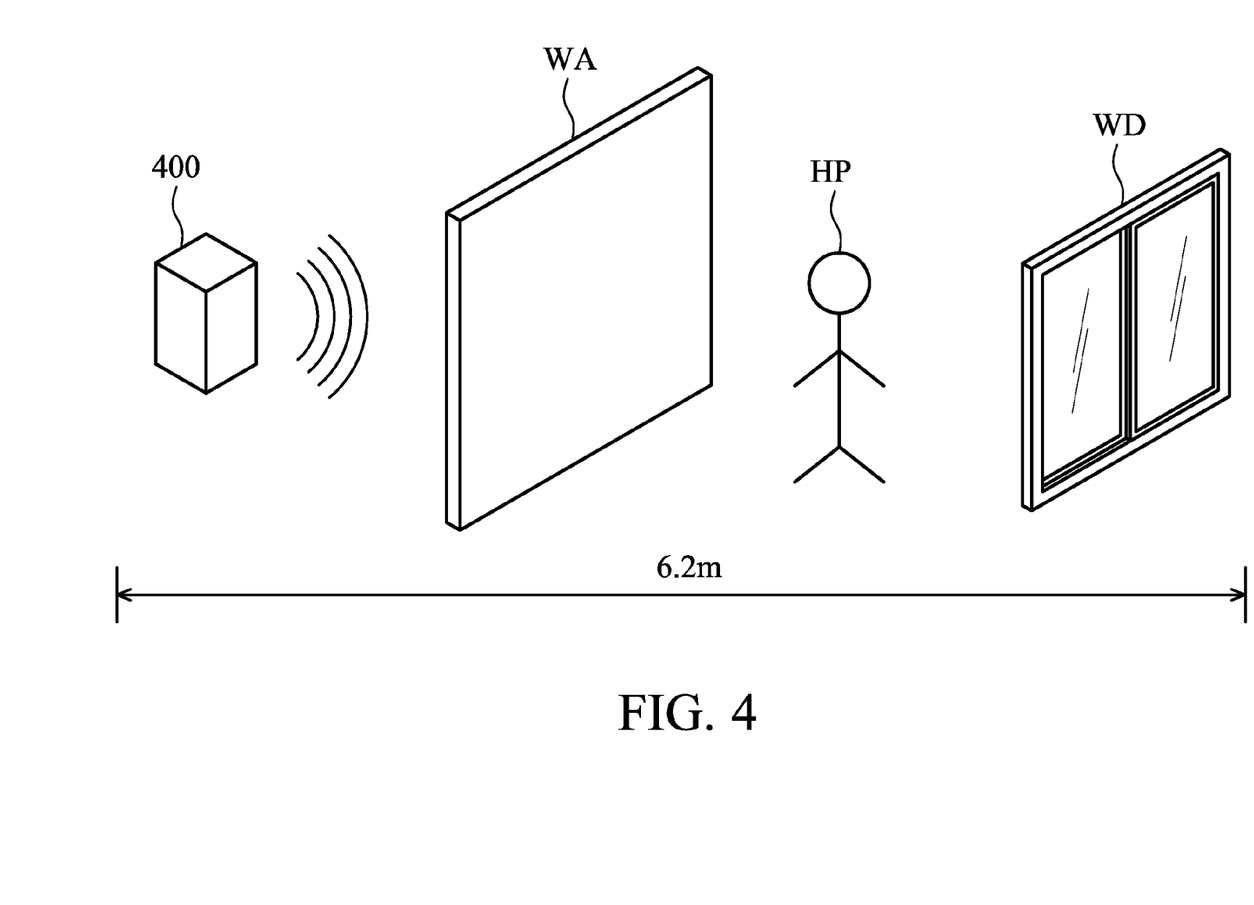
FIG. 4 is a schematic diagram illustrating a detection of a hidden person of the disclosure.

FIG. 4 is a schematic diagram illustrating a detection of a hidden person of the disclosure. As shown in FIG. 4, there is a hidden person HP between a wood wall WA and a window WD. The wireless detection device 400 is the same as the wireless detection devices 100, 200 and 300, and is configured to detect whether there is a person behind the wood wall WA. In an embodiment, the analog control voltages Vt is a ramp signal with 200 Hz, so the frequency of the oscillation signals Sosc varies between 2.4-2.484 Ghz, such that the voltage control oscillation unit 30 performs a swept frequency procedure. Note that the transmission delay time in the circuit is about 18 ns, the distance between the hidden person HP and the wireless detection device 400 is 4 meters, and the distance between the window WD and the wireless detection device 400 is 6.2 meters.

Figure 5:
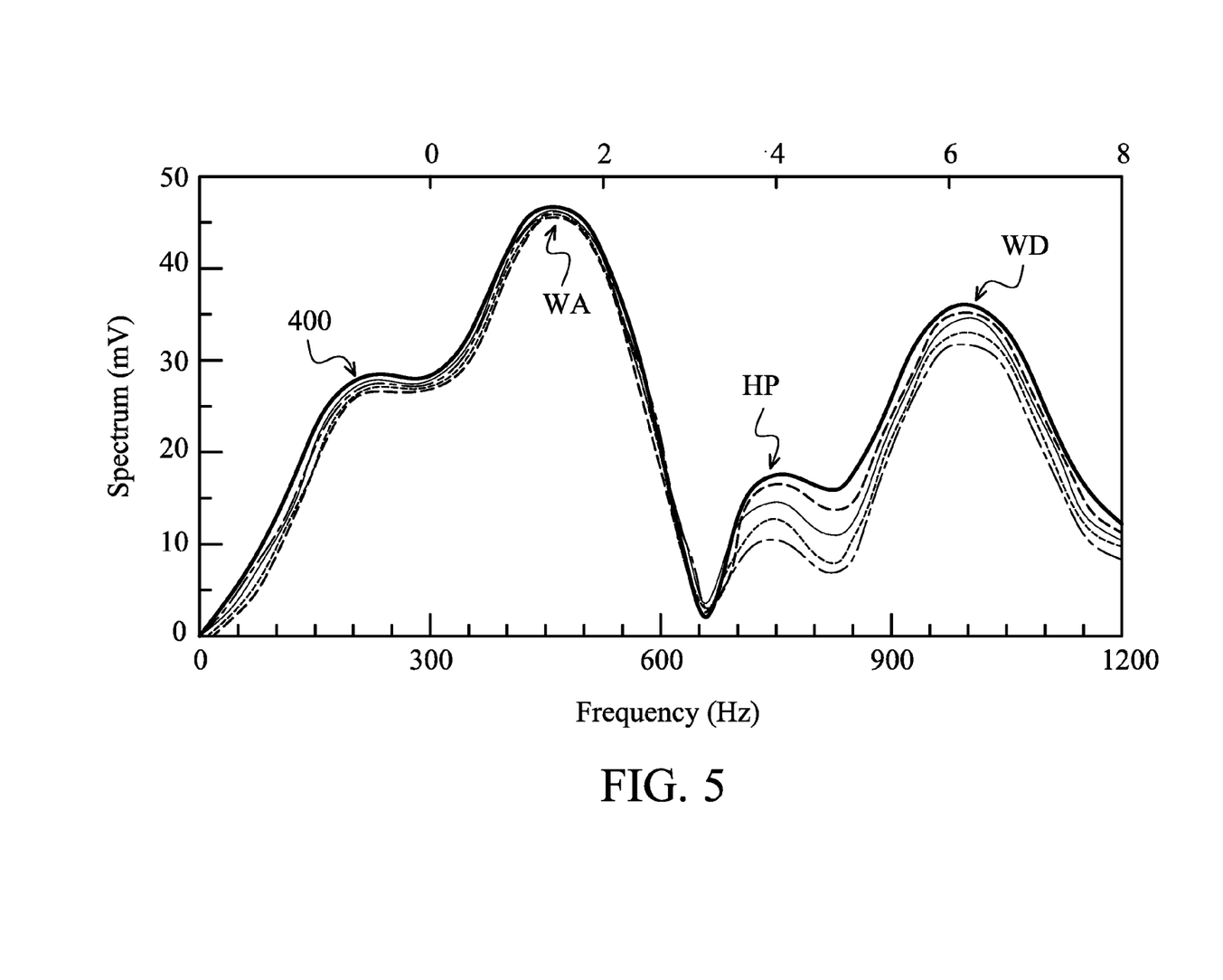
FIG. 5 is a spectrum of the second voltage signals SV2 of the disclosure.

FIG. 5 is a spectrum of the second voltage signals SV2 of the disclosure. As shown in FIGS. 4 and 5, the second voltage signal SV2 has peak value when its frequency meets 225 Hz, 460 Hz, 740 Hz and 1000 Hz. The relation between the real distance and frequency is $$R = c\left(\frac{\omega}{4\pi S} - \tau\right)$$

(Formula 1), wherein R is the real distance, $\omega$ is frequency, $\tau$ and c are constant, and S is swept frequency rate. Therefore, the processing unit 80 can calculate the real distance as 0 meters, 1.43 meters, 4 meters and 6.2 meters according to the frequency 225 Hz, 460 Hz, 740 Hz and 1000 Hz, respectively, and the result of calculating matches FIG. 4.

Figure 6:
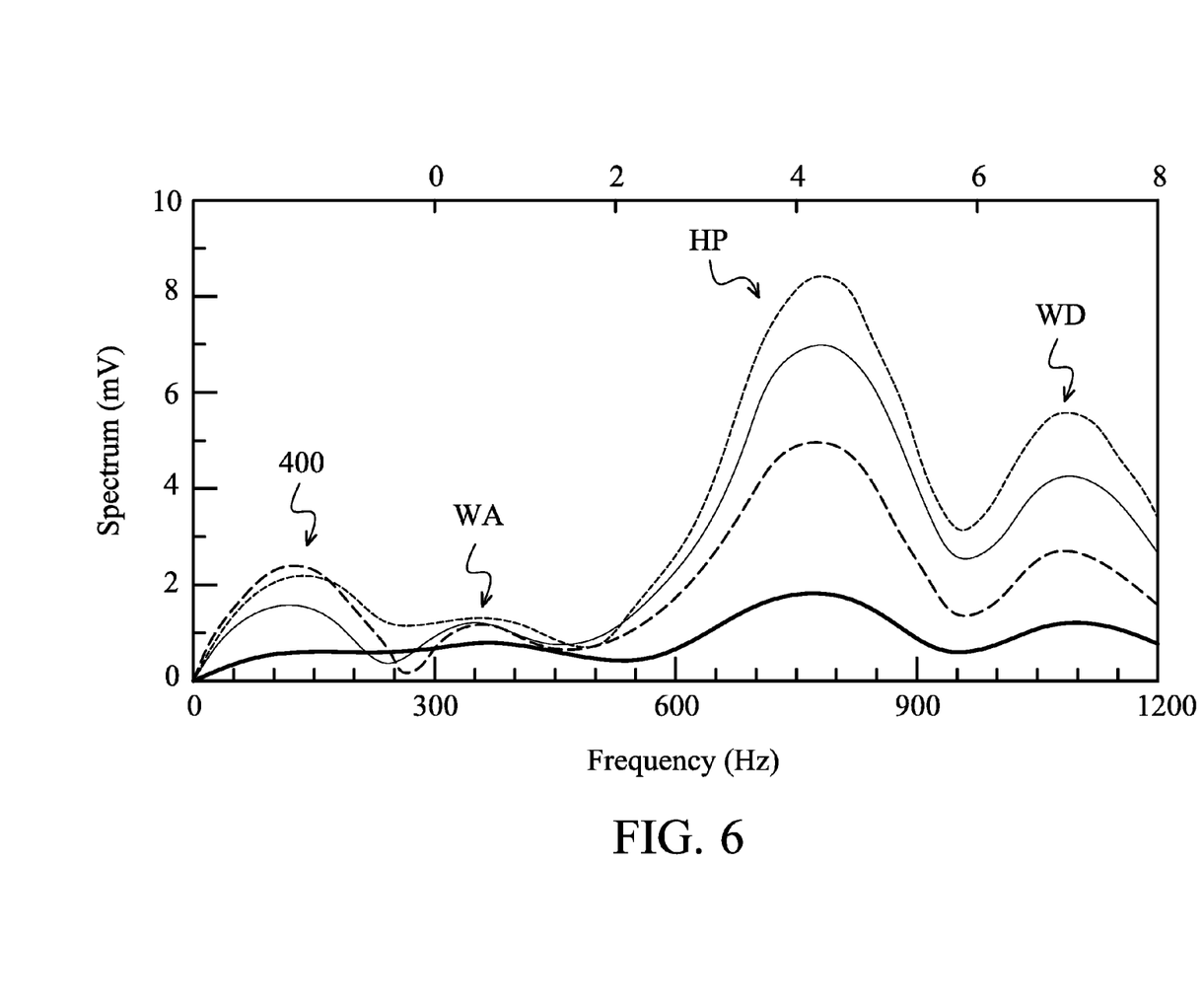
FIG. 6 is a spectrum of the variation of the second voltage signals SV2 at different times of the disclosure.
Figure 7:
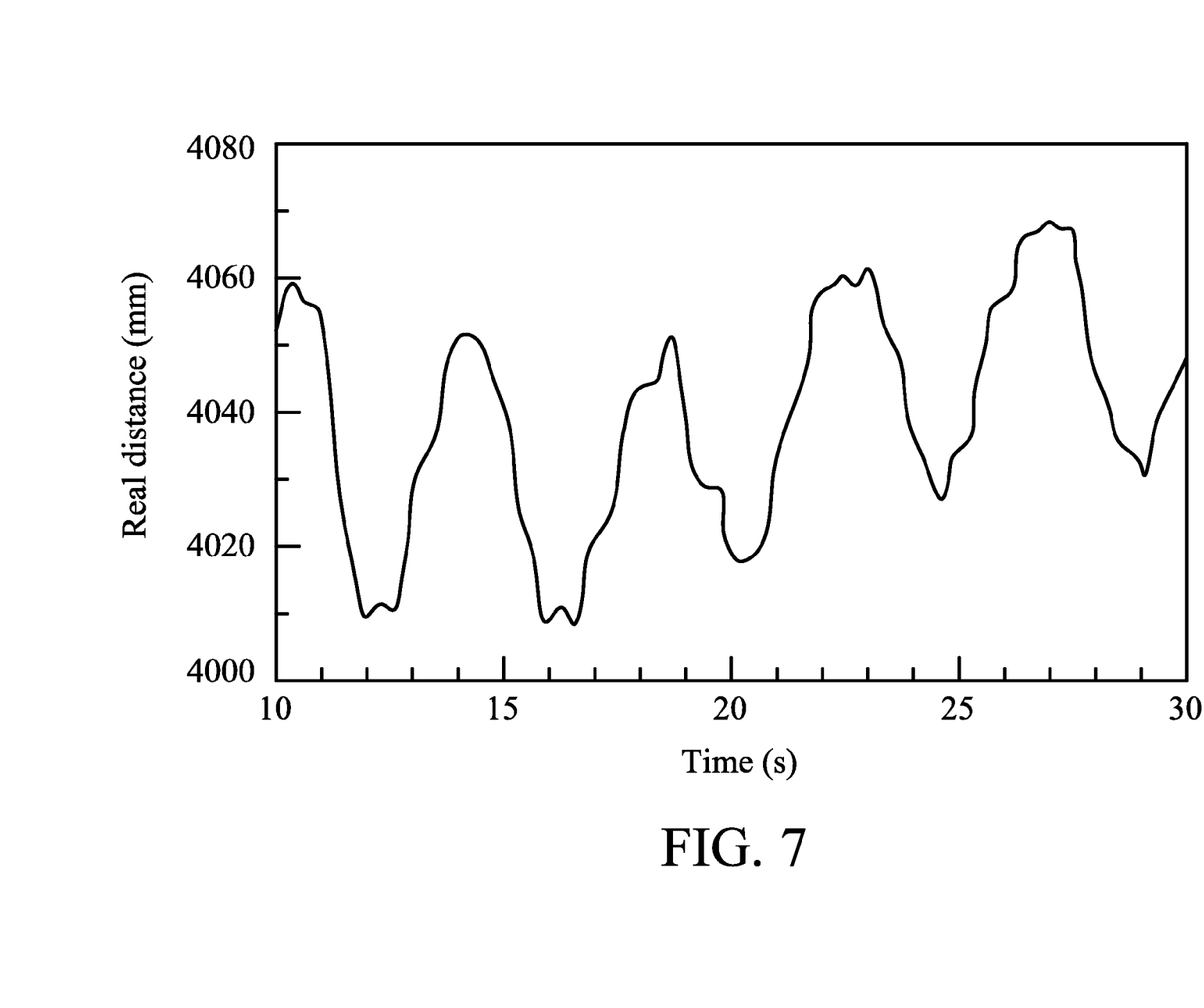
FIG. 7 is a diagram illustrating the relation between the real distance of the hidden human HP and time.
Figure 8:
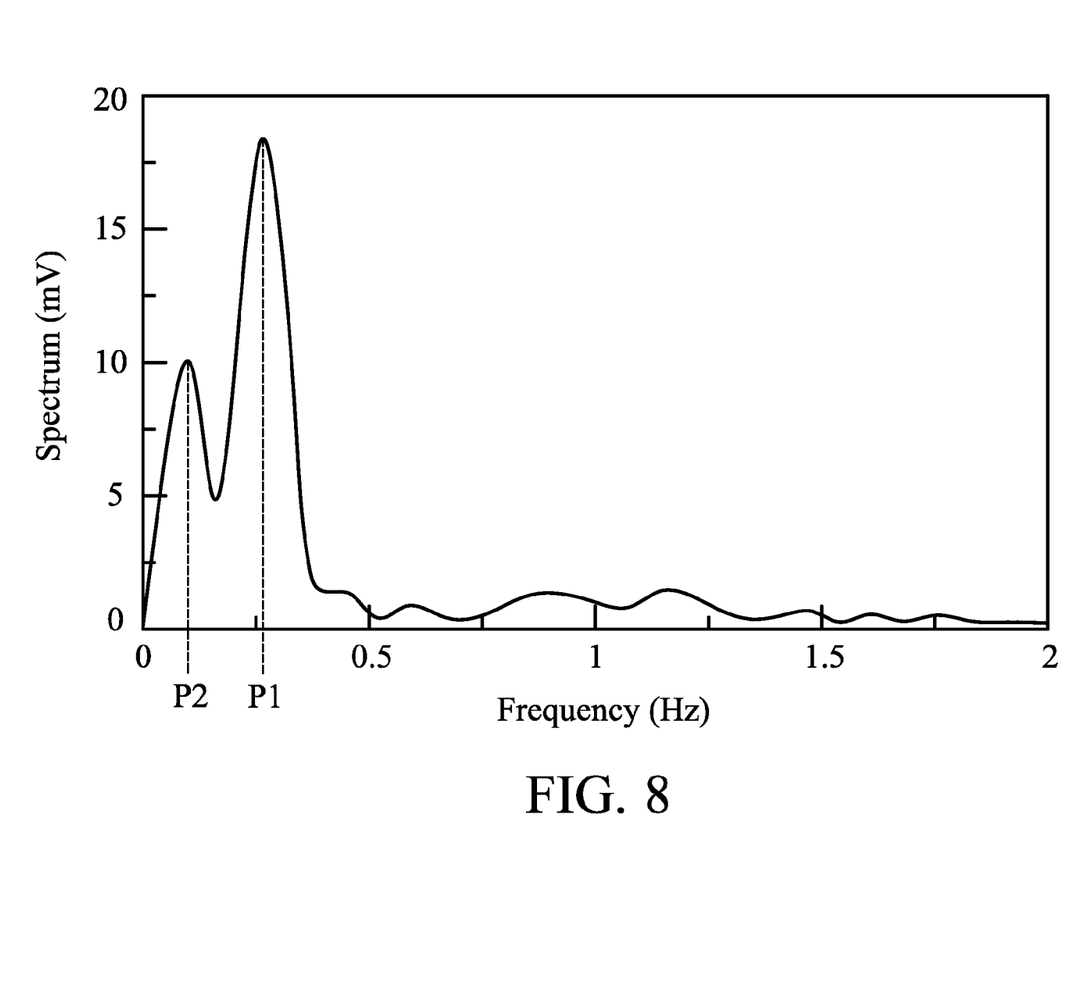
FIG. 8 is another spectrum of the disclosure.

FIG. 6 is a spectrum of the variation of the second voltage signals SV2 of the disclosure at different times. As shown in FIG. 6, the vibration of the hidden human HP causes the variation of the second voltage signals SV2 to exceed a predetermined value. FIG. 7 is a diagram illustrating the relation between the real distance of the hidden human HP and time. As shown in FIG. 7, due to the physiology frequency (for example, a heartbeat frequency or a breathing frequency) of the hidden human HP, the real distance of the hidden human HP varies periodically. Therefore, the processing unit 90 confirms whether the detected object is an organism according to a variation frequency of the real distance. FIG. 8 is another spectrum of the disclosure, and is the Fourier transform of the FIG. 7. As shown in FIG. 8, point P1 indicates the breathing frequency of the hidden human HP The breathing frequency is about 0.26 Hz, and point 2 indicates the frequency of slow move of the hidden human HP.

Figure 9:
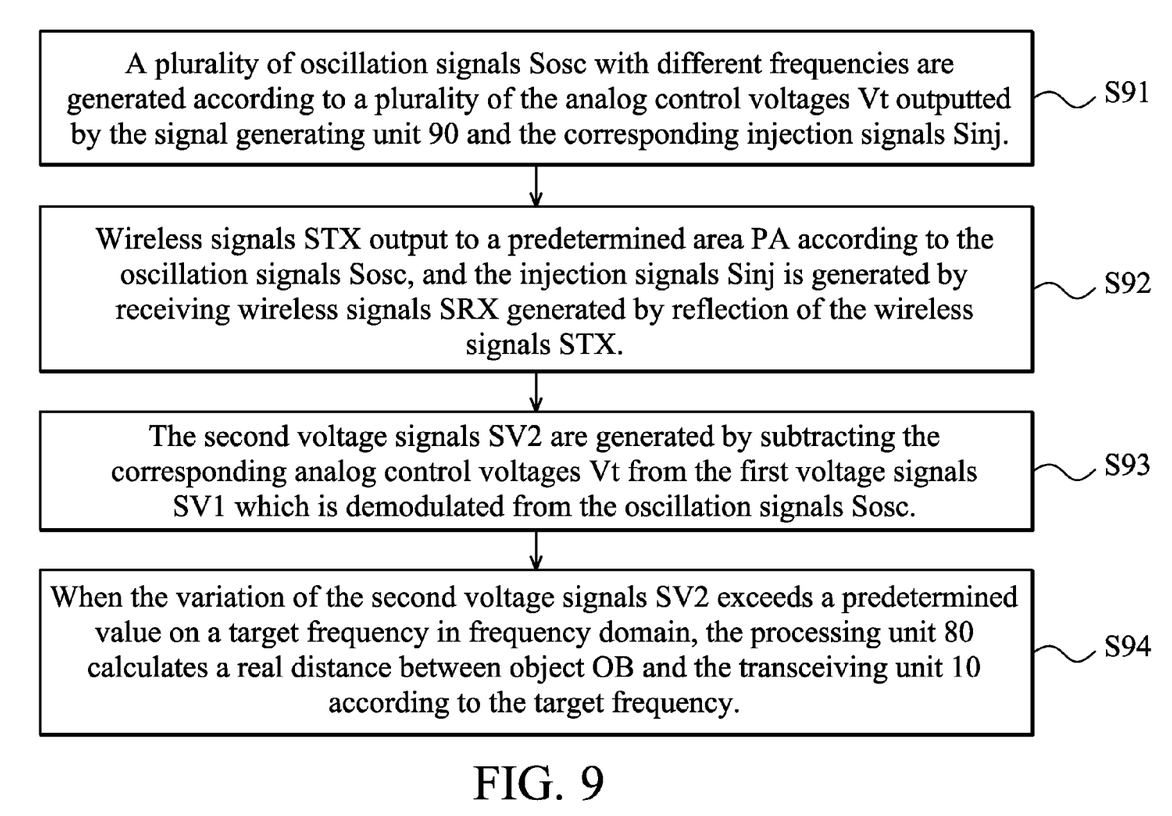
FIG. 9 illustrates a flowchart of a wireless detection method of the disclosure.

FIG. 9 illustrates a flowchart of a wireless detection method of the disclosure. As shown in FIG. 9 the wireless detection method includes the following steps.

In step S91, a plurality of oscillation signals Sosc with different frequencies are generated according to a plurality of the analog control voltages Vt outputted by the signal generating unit 90 and the corresponding injection signals Sinj. In step S92, wireless signals STX are output to a predetermined area PA according to the oscillation signals Sosc, and the injection signals Sinj are generated by receiving the wireless signals SRX generated by reflection of the wireless signals STX.

In step S93, the second voltage signals SV2 are generated by subtracting the corresponding analog control voltages Vt from the first voltage signals SV1 which are demodulated from the oscillation signals Sosc. In step S94, when the variation of the second voltage signals SV2 exceeds a predetermined value on a target frequency in frequency domain, the processing unit 80 calculates a real distance between the object OB and the transceiving unit 10 according to the target frequency.

Note that in the other possible embodiments, the demodulation unit can be performed by means other than the embodiment of the FIG. 3. FIGS. 10A-10D illustrate the other embodiments of the demodulation units according to the disclosure.

Figure 10A:
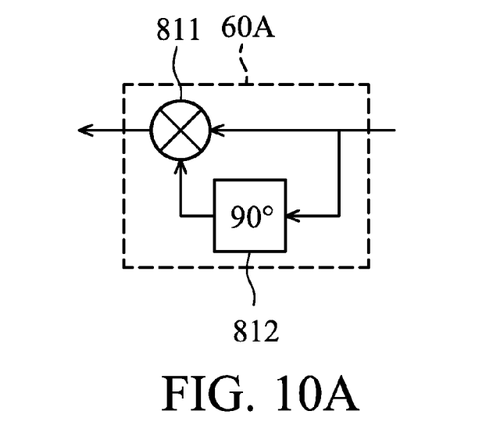
FIG. 10A illustrates the other embodiments of the demodulation units according to the disclosure.

In FIG. 10A, the demodulation unit 60A is a quadrature demodulator, and the demodulation unit 60A comprises a mixer 811 and a phase shifting unit 812. The phase shifting unit 812 adjusts the phase of the inputted oscillation signals Sosc to generate 90 degrees of phase difference of the input signal and the output signal. The mixer 811 obtains a demodulation signal by multiplying the inputted oscillation signals Sosc and the output signal from the phase shifting unit 812 together.

Figure 10B:
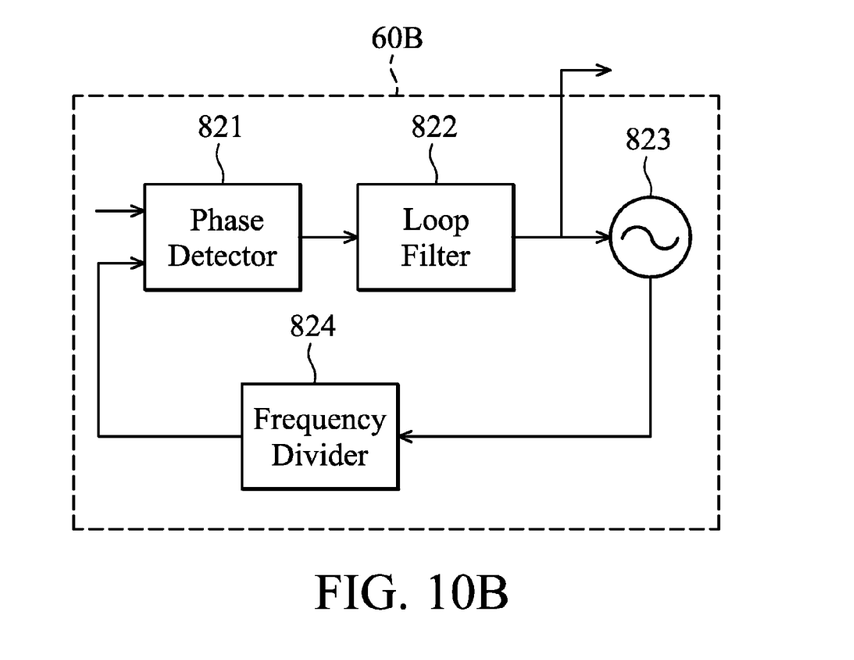
FIG. 10B illustrates the other embodiments of the demodulation units according to the disclosure.

In FIG. 10B, the demodulation unit 60B is a PLL demodulator, and the demodulation unit 60B comprises a phase detector 821, a loop filter 822, a voltage control oscillator 823 and a frequency divider 824. The arrangement of the FIG. 10B is similar to Phase-Locked Loops, so it is named as PLL demodulator. The phase detector 821 compares the phases between the inputted oscillation signals Sosc and the signals generated by the voltage control oscillator 823/the frequency divider 824, and the loop filter 822 performs loop filtering according to the phase comparison result of the phase detector 821 to generate a frequency control voltage. The frequency control voltage locks the frequency of the voltage control oscillator 823 in order to synchronize the inputted oscillation signals Sosc and the output signal of the voltage control oscillator 823. The frequency control voltage is frequency modulation information of the oscillation signals Sosc.

Figure 10C:
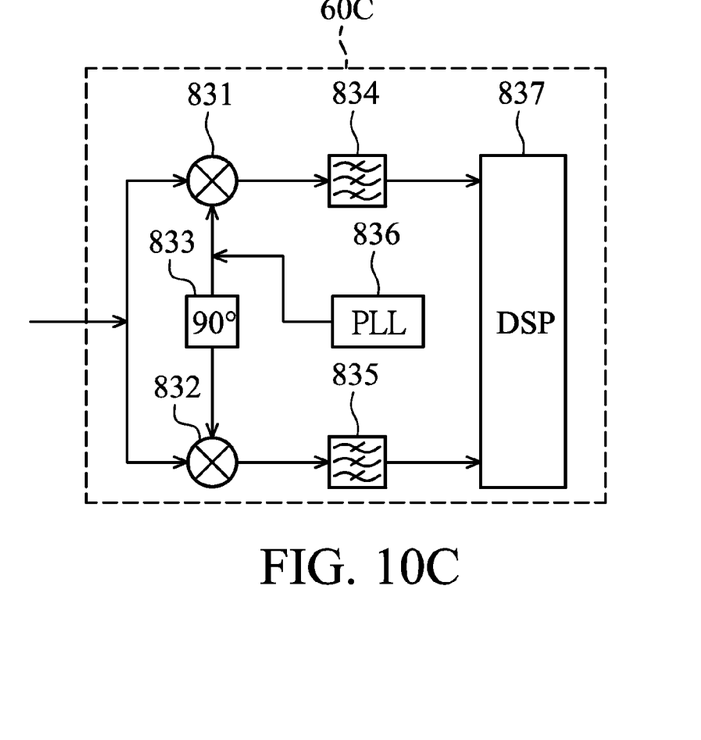
FIG. 10C illustrates the other embodiments of the demodulation units according to the disclosure.

In FIG. 10C, the demodulation unit 60C is a synchronous demodulator or an IQ-demodulator. The demodulation unit 60C comprises a mixer 831, a mixer 832, a phase shifting unit 833, a low pass filer 834, a low pass filer 835, a phase-locked loop 836 and a digital signal processor (DSP) 837. The inputted oscillation signals Sosc are input to the mixer 831 and the mixer 832 respectively. Each switch stage signal of the mixer 831 and the mixer 832 is provided by the phase-locked loop 836, but the phase difference between the switch stage signals is 90 degrees. After the cross modulation signals are filtered out of the output signals of the mixer 831 and the mixer 832 by the low pass filer 834 and low pass filer 835 respectively, and digital signal processor 837 obtains frequency modulation information accordingly.

Figure 10D:
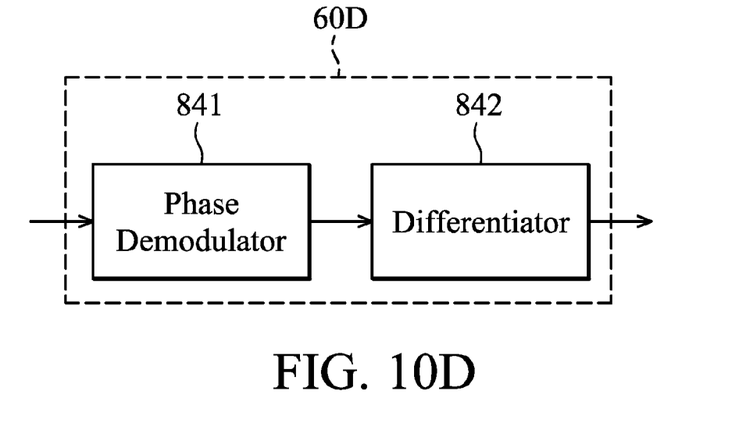
FIG. 10D illustrates the other embodiments of the demodulation units according to the disclosure.

In FIG. 10D, the demodulation unit 60D comprises a phase demodulator 841 and a differentiator 842. The inputted oscillation signals Sosc are input to the phase demodulator 841 in order to obtain the phase variation. The differentiator 842 obtains frequency modulation information by differentiating.

Due to the wireless detection device and the wireless detection method of the disclosure, whether there is an organism behind a barrier (such as a wall) can be detected, and the processing unit 80 can confirm the type of the object according to a variation frequency of the real distance. For example, when the variation frequency is a physiology frequency of a human body (such as a heartbeat frequency or a breathing frequency), the processing unit 80 determines that the object is a human body. When the variation frequency is not the physiology frequency of a human body (such as a motor frequency), the processing unit 80 determines that the object is a motor or the other organism. Also, when the second voltage signal SV2 does not exceed a predetermined value on a target frequency in frequency domain, the processing unit 80 determines that there is no organism behind the wall WA.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A wireless detection device, comprising:
  a voltage control oscillation unit, generating a plurality of oscillation signals with different frequencies according to analog control voltages;
  a transceiving unit, outputting a plurality of first wireless signals to an object in a predetermined area according to the oscillation signals, and receiving second wireless signals generated by reflection of the first wireless signals to yield self-injection-locking signals for modulating the voltage control oscillation unit;
  a demodulation unit, configured to demodulate the oscillation signals into first voltage signals;
  a signal generating unit, configured to generate the analog control voltages; and
  a processing unit, subtracting the corresponding analog control voltages from the first voltage signals to generate second voltage signals,
  wherein when the variation of the second voltage signals in frequency domain exceeds a predetermined value on a target frequency, the processing unit calculates a distance between the object and the transceiving unit and further a variation frequency of the distance according to the target frequency, wherein the processing unit further comprises:
    a first subtractor, connected to the signal generating unit and the demodulation unit, and configured to subtract the corresponding analog control voltages from the first voltage signals to generate the second voltage signals;
    a first calculating unit, connected to the first subtractor, and configured to transform the second voltage signals into frequency domain;
    a storage unit, configured to store spectra of the transformed frequency domain of the second voltage signals at different times;
    a second subtractor, connected to the storage unit, and configured to obtain a difference between the spectra of the second voltage signals; and
    a second calculating unit, connected to the storage unit, and configured to transform the time-varying spectra into the variation frequency of the distance.

2. The wireless detection device of claim 1, further comprising:
a low pass filter, connected between the demodulation unit and the processing unit, and configured to filter a high frequency noise.

3. The wireless detection device of claim 1, wherein the transceiving unit further comprises:
a first antenna, configured to output the first wireless signals to the object;
a second antenna, configured to receive the second wireless signals reflected by the object;
a first amplifier, connected between the second antenna and the voltage control oscillation unit, and configured to amplify the second wireless signals into the self-injection-locking signals; and
a second amplifier, connected between the first antenna and the voltage control oscillation unit, and configured to amplify the oscillation signals into the first wireless signals.

4. The wireless detection device of claim 1, wherein the demodulation unit further comprises:
a delayer, connected to the voltage control oscillation unit, and configured to delay the oscillation signals; and
a mixer, connected to the voltage control oscillation unit and the delayer, and configured to generate the first voltage signals by mixing the oscillation signals and the delayed oscillation signals.

5. The wireless detection device of claim 3, wherein the processing unit further comprises:
a third amplifier, connected to the signal generating unit, and configured to amplify the analog control voltages.

6. The wireless detection device of claim 1, wherein the processing unit confirms a type of the object according to the variation frequency.

7. The wireless detection device of claim 6, wherein when the variation frequency is a physiology frequency, the processing unit determines the object as a human body.

8. The wireless detection device of claim 7, wherein the physiology frequency is a heartbeat frequency or a breathing frequency.

9. A wireless detection method for a wireless detection device, the wireless detection method comprising:
generating a plurality of oscillation signals with different frequencies by a voltage control oscillation unit of the wireless detection device according to analog control voltages outputted by a signal generating unit of the wireless detection device;
outputting a plurality of first wireless signals to an object in a predetermined area according to the oscillation signals, and receiving second wireless signals generated by reflection of the first wireless signals to yield self-injection-locking signals for modulating the voltage control oscillation unit;
generating second voltage signals by subtracting the corresponding analog control voltages from first voltage signals, wherein the first voltage signals are demodulated from the oscillation signals;
transforming the second voltage signals into frequency domain;
storing spectra of the transformed frequency domain of the second voltage signals at different times;
obtaining a difference between the spectra of the second voltage signals;
when the difference between the spectra of the second voltage signals exceeds a predetermined value on a target frequency, transforming the time-varying spectra into a variation frequency of the distance; and
analyzing the variation frequency of the distance by a processing unit of the wireless detection device.

10. The wireless detection method of claim 9, wherein the processing unit confirms a type of the object according to the variation frequency of the distance.

11. The wireless detection method of claim 9, wherein when the variation frequency is a physiology frequency, the processing unit determines the object as a human body.

12. The wireless detection method of claim 11, wherein the physiology frequency is a heartbeat frequency or a breathing frequency.

* * * * *